(12) United States Patent
Toyo-Oka

(10) Patent No.: US 6,589,523 B2
(45) Date of Patent: Jul. 8, 2003

(54) AGENT FOR GENE THERAPY OF DILATED CARDIOMYOPATHY

(76) Inventor: Teruhiko Toyo-Oka, 23-3, Kamiogi 3-chome, Suginami-ku, Tokyo 167-0043 (JP)

( * ) Notice: Subject to any disclaimer, the term of this patent is extended or adjusted under 35 U.S.C. 154(b) by 4 days.

(21) Appl. No.: 09/768,807

(22) Filed: Jan. 25, 2001

(65) Prior Publication Data

US 2001/0029040 A1 Oct. 11, 2001

Related U.S. Application Data

(60) Provisional application No. 60/183,331, filed on Feb. 18, 2000.

(30) Foreign Application Priority Data

Feb. 23, 2000 (JP) ........................................ 2000-045387

(51) Int. Cl.$^7$ ........................ A01H 63/00; A01H 43/04; A01K 48/00; A01K 31/70; C12P 21/06; C12N 5/00; C12N 15/00; C12N 15/63

(52) U.S. Cl. ................. 424/93.2; 424/93.21; 424/93.1; 435/69.1; 435/320.1; 435/325; 435/455; 514/44; 536/23.1; 536/23.5

(58) Field of Search ............................. 435/69.1, 320.1, 435/325, 455; 536/23.1, 23.5; 514/44; 424/93.2, 93.21, 93.1

(56) References Cited

U.S. PATENT DOCUMENTS 4,797,368 A 1/1989 Carter et al.
6,262,035 B1 * 7/2001 Campbell et al. ............. 514/44

OTHER PUBLICATIONS

Li et al., rAAV vector–mediated sarcoglycan gene transfer in a hamster model for limb gridle muscular dystrophy, Jan. 1999, Gene Therapy, vol. 6, No. 1, pp. 74–82.*
Tomie Kawada et al, Morphological and Physiologial Restorations of Hereditary Form of Dilated Cardiomyopathy by Somatic Gene Therapy, 284, 431–435 (2001).*

Leon E. Rosenberg et al, Gene Therapist, Heal Thyself, Science vol. 287, Mar. 10, 2000.*
Inder M. Verma, Gene Therapy: Beyond 2000, Molecular Therapy vol. 1, No. 6, Jun. 2000.*
Theodore Friedmann, Principles for Human Gene Therapy Studies, Science vol. 287, Mar. 24, 2000.*
W. French Anderson, Human gene therapy, Nature vol. 392, April 30, 1998.*
Inder M. Verma et al, Gene therapy–promises, problems, and prospects, nature vol. 389, Sep. 18, 1997.*
Sakamoto et al., "Both Hypertrophic and Dilated Cardiomyopathies are caused by Mutation of the Same Gene, δ–sarcoglycan, in Hamster: An animal Model of Disrupted Dystropin–Associated Glycoprotein Complex", *Proc. Natl. Acad. Sci.*, vol. 94, pp. 13873–13878 (1997).
Abstract of Kawada et al., Strain– and Age–Dependent Loss of Sarcoglycan Complex in Cardiomyopathic Hamster Hearts and its Re–expression by Delta–Sarcoglycan Gene Transfer in Vivo; FEBS Lett, 458(3), pp. 405–408 (1999).
Kawaguchi et al., "In Vivo Gene Transfection of Human Endothelial Cell Nitric Oxide Synthase in Cardiomyocytes Causes Apoptosis–Like Cell Death", *Circulation*, 95:2441–2447 (1997).
Tsubata et al., "Mutations in the δ—sarcoglycan gene in familial and sporadic dilated cardiomyopathy", *The Journal of Clinical Investigation*, vol. 106, pp. 655–622 (2000).
Abstract of Kay et al., "Evidence for Gene Transfer and Expression of Factor IX in Haemophilia B Patients Treated with an AAV Vector", *Nat Genet* 24(3), pp. 257–261 (2000).

* cited by examiner

*Primary Examiner*—Jeffrey Fredman
*Assistant Examiner*—Sumesh Kaushal
(74) *Attorney, Agent, or Firm*—Greenblum & Bernstein, P.L.C.

(57) ABSTRACT

According to the present invention, there is provided a gene expression vector which is obtained by inserting a gene encoding sarcoglycan into an adeno-associated virus (AAV) vector. By administering the gene expression vector of the present invention to a living body in vivo, a sarcoglycan can be continuously expressed in the living body, so that the restoration of α-, β-, γ- and δ-sarcoglycan components can be accompanied and the heart function of the patient of dilated cardiomyopathy can be improved.

8 Claims, 5 Drawing Sheets

AGENT FOR GENE THERAPY OF DILATED CARDIOMYOPATHY

CROSS-REFERENCE TO RELATED APPLICATION

The present application claims the priority under 35 U.S.C. §119(e) of U.S. Provisional Application No. 60/183,331, filed Feb. 18, 2000, the disclosure of which is expressly incorporated by reference herein in its entirety.

TECHNICAL FIELD

The present invention relates to an agent for gene therapy of dilated cardiomyopathy, more particularly, a gene expression vector which is obtained by inserting a gene encoding a sarcoglycan into an adeno-associated virus vector.

BACKGROUND ART

Cardiomyopathy is one of the heart diseases which shows contraction dysfunction and electrophysiological dysfunction as symptoms, and includes a group of heart diseases which lead to a sever heart failure and a sudden death. Cardiomyopathy is classified into dilated cardiomyopathy and hypertrophied cardiomyopathy, and the study for revealing the causes of each cardiomyopathy has been made. In the case of dilated cardiomyopathy (DCM), in spite of progress in the therapy, the prognosis of the patients is still poor and cardiac transplantation is necessary in the deteriorated cases (V. V. Michels, et al., New Engl.J.Med. 326, 77 (1992); E. K. Kasper, et al., J.Am.Coll.Cardiol. 23, 586 (1994); M. Packer, et al., New Engl.J.Med. 334, 1349 (1996); M. Packer, et al. New Engl.J.Med. 335,1107 (1996); R. M. Graham, W. A. Owens, N.Engl.J.Med. 341, 1759 (1999)). Therefore, it is necessary to develop a novel method for therapy which can improve the patient's mortality and morbidity. Animal model is useful for developing such a novel method for therapy.

Gene transfer will be promising for the therapy of some type of DCM which is caused by the gene deletion. It has been demonstrated that the deletion of δ-sarcoglycan (δ-SG) gene is the cause of DCM in hamsters (A. Sakamoto, et al., Proc.Natl.Sci.Acad.U.S.A. 94, 13873 (1997); V. Nigro, et al., Hum.Mol.Genet. 6, 601 (1997)). Also, it has been found that the breakpoint of δ-SG gene in TO-2 hamster which is a model animal of DCM is present in the first intron, and large region including its promoter and the first exon is deleted in TO-2 hamster (A. Sakamoto, et al., Proc.Natl.Sci.Acad.U.S.A. 94, 13873 (1997)). Furthermore, dystrophin-associated glycoprotein complex (DAGC) links intracellular contractile machinery with extracellular matrix (G. F. Cox, L. M. Kunkel, Curr.Opin.Cardiol. 12, 329 (1997); K. H. Holt, et al., Mol. Cell 1, 841 (1998); M. D. Henry, K. P. Campbell, Curr.Opin.Cell Biol. 11, 602 (1999)).

The δ-SG makes a complex with the other three SGs (α-, β-, γ-SG) and connects intracellular dystrophin with laminin-2 at the extracellular matrix via α- and β-dystroglycans (G. F. Cox, L. M. Kunkel, Curr.Opin.Cardiol. 12, 329 (1997); K. H. Holt, et al., Mol.Cell 1, 841 (1998); M. D. Henry, K. P. Campbell Curr.Opin. Cell Biol. 11, 602 (1999)). In the myocardium of TO-2 hamster, the expressions of all of α-, β-, γ- and δ-SGs are missing in contrast with the myocardium of BIO 14.6 hamster (a model animal of hypertrophied cardiomyopathy) (T. Kawada, et al., F.E.B.S.Lett. 45, 405 (1999); T. Kawada, et al., Biochem.Biophys.Res.Commun. 259, 408 (1999)).

As one of the means for the therapy of heart diseases caused by the gene deletion or the change of gene expression in diseased cardiac muscle tissues such as dilated cardiomyopathy, molecular biological methods such as a direct transfer of gene into somatic cells of cardiac muscle tissues have been proposed.

Various methods have been proposed for gene transfer into somatic cells. For example, there have been proposed a gene transfer by DNA injection, a gene transfer using liposome, a gene transfer using a retrovirus vector, an adenovirus vector or an adeno-associated virus vector and the like. Important factors for the success of gene therapy include a high transfer efficiency, a stable expression of the gene, a tissue specificity, and a high safety to host.

For example, it has been proposed that a retrovirus vector is used for gene therapy. However, the use of retrovirus vector has many disadvantages. For example, virus DNA is randomly inserted into the chromosome of the host, and mutations may occur by such an insertion. In addition, the LTR (long terminal repeat) structure present in both ends of the retrovirus genome has a promoter/enhancer activity, and this activity may cause an activation of a gene locus which is adjacent to the inserted virus DNA.

As to those other than retrovirus, for example, adeno-associated virus (AAV) is studied as another system for delivering gene information into cells. The construction of a recombinant vector which comprises AAV DNA and heterogeneous gene under the control of AAV transcription promoter is described in, for example, U.S. Pat. No. 4,797,368 of Carter et al.

However, even in the case of using AAV vector, the gene therapy does not always succeed by satisfying various factors such as a high infection efficiency, a stable expression of the gene, a high tissue specificity, and a high safety. Especially, it has not been reported that the heart function of the patients of dilated cardiomyopathy can be improved by administering a gene expression vector into heart in vivo.

DISCLOSURE OF INVENTION

Thus, an object of the present is to construct a gene expression vector which can be used for a gene therapy of the patients of dilated cardiomyopathy.

Another object of the present invention is to construct a gene expression vector which can stably express a gene of interest when it is directly injected into the heart of the patients of dilated cardiomyopathy.

Still another object of the present invention is to construct a gene expression vector which can improve the heart function of the patients of dilated cardiomyopathy when it is directly injected into the heart of said patients.

Still another object of the present invention is to provide a pharmaceutical composition for gene therapy which comprises the aforementioned gene expression vector.

The present inventor has diligently studied to solve the aforementioned problems, and employed 5 week-old male TO-2 hamsters as a model animal (T. Kawada, et al., F.E.B.S.Lett. 45, 405 (1999); T. Kawada, et al., Biochem.Biophys.Res.Commun. 259, 408 (1999)), and employed a recombinant adeno-associated virus (rAAV) as a gene transfer vector, and injected δ-SG gene into the heart of TO-2 hamster in vivo. As a result, it has been found that the heart function is improved in TO-2 hamster where δ-SG gene has been transferred, and the present invention has been completed.

Thus, according to the present invention, there is provided a gene expression vector which is obtained by inserting a gene encoding sarcoglycan into an adeno-associated virus (AAV) vector.

Preferably, sarcoglycan is δ-sarcoglycan.

Preferably, the gene encoding sarcoglycan is a hamster or human sarcoglycan gene.

The gene expression vector of the present invention is preferably used for the therapy of heart diseases caused by deletion of sarcoglycan gene, particularly preferably dilated cardiomyopathy.

According to another aspect of the present invention, there is provided a pharmaceutical composition for gene therapy which comprises the gene expression vector of the present invention.

The pharmaceutical composition for gene therapy of the present invention is preferably used for the therapy of heart diseases caused by deletion of sarcoglycan gene, particularly preferably dilated cardiomyopathy.

DETAILED DESCRIPTION OF INVENTION

Figure 1:
FIG. 1(A) represents the results of RNA blot analysis of δ-sarcoglycan (SG) for left ventricle. 2 μg poly (A)+RNA per lane was used. Lane C represents control normal strain; Lane T represents TO-2 hamster without gene transfer; and Lane T+ represents hamster at 10 weeks after the gene transfer to 5-week-old hamsters by an rAAV-mediated vectors. The δ-SG transcripts of 4.4 kb band is that of transferred TO-2 (T+) and persisted for at least 20 weeks. The transcript size was larger than that of endogenous δ-SG mRNA detected in normal hamsters.
FIG. 1(B) represents the results of histological examination of gene-transfected region. Hematoxylin-eosin staining of cryostat section sampled at 10 weeks after the in vivo cotransfer of Lac Z and δ-SG gene is shown. Bar length at right lower part indicates 1 mm.
Figure 1:
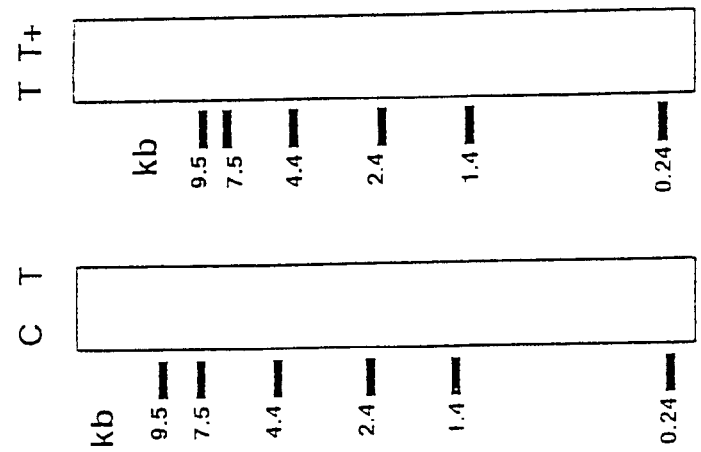

The practices and embodiments of the present invention are described below. The disclosures of the references cited herein are incorporated herein by reference, and the disclosures of the references are considered to be a part of the disclosures of this specification. Also, the disclosures of Japanese Patent Application No. 2000-45387 and U.S. Provisional Application No. 60/183,331 which are the basic applications of the priorities which the present application claims, are incorporated herein by reference.

(A) Gene Expression Vector Comprising SG Gene

The present invention relates to a gene expression vector which is obtained by inserting a gene encoding sarcoglycan into an adeno-associated virus (AAV) vector.

1. AAV Vector

"Gene expression vector" used herein is a nucleic acid construct which can express a gene of interest (a gene encoding sarcoglycan). The vector may generally be composed of DNA or RNA, and an adeno-associated virus (AAV) vector is used in the present invention.

The adeno-associated virus (AAV) vector is a deficient parvovirus composed of a linear single-strand DNA molecule of 4680 nucleotides, and contains an open reading frame which encodes REP (replication) protein and CAP (capsid) protein. REP proteins function at the time of virus replication, and CAP proteins are assembled to form a virus capsid molecule which packages the virus genome. 2 ITRS (inverted terminal repeat sequence) of 145 nucleotides are adjacent to AAV coding region, and this sequence contains a palindrome sequence which is fold to form a hairpin structure and functions as a primer at the time of DNA replication. It has been demonstrated that ITR sequence is necessary for DNA replication, as well as for virus integration, rescue from host genome, and capsid encompassment of virus nucleic acid into mature virion (Muzyczka, N., 1992, Current Topics in Microbiology & Immnunology 158:97–129).

In the presence of helper virus, AAV enters into a bacteriolytic route, so that the virus genome is transcribed and replicated, and it is encompassed into capsid to form new virus particles. In the absence of helper virus function, AAV genome is integrated into the genome of the host cell as a provirus by means of recombination between both ends of AAV and the sequence of the host cell (Cheung, A. et al., 1980, J. Virol. 33:739–748; Berns, K. I. et al, 1982, in Virus Persistence, Mahey, B. W. J. et al, ed. (Canmbridge Univ. Press, Cambridge), pp. 249–265). As a result of the analysis of integration site of provirus and the analysis of the sequence of the host cell which is adjacent to the integration site, it is suggested that a wild-type AAV virus DNA is specifically targeted into the long arm of human chromosome 19 (Kotin, R. M. et al., 1990, Proc. Natl. Acad. Sci.

USA 87:2211–2215; Samulski, R. J. et al., 1991, EMBO J. 10:3941–3950).

As AAV vector, an adeno-associated virus type 1 (AAV-1) and an adeno-associated virus type 2 (AAV-2) vectors (WO95/13365; Flotte et al., PNAS 90(22):10613–10617, 1993) are known. The method for use of such vectors in gene therapy is known in the art (for example, Larrick, J. W. and Burck, K. L., Gene Therapy: Application of Molecular Biology, Elsevier Science Publishing Co., Inc., New York, N.Y., 1991; and Kreigler, M., Gene Transfer and Expression: A Laboratory Manual, W. H. Freeman and Company, New York, 1990)

As AAV vector for use in the present invention, various types of AAV vector can be used. For example, AAV vector contains AAV virus sequence which lacks REP and/or CAP gene. Also, the recombinant vector may contain bacteria plasmid sequence necessary for providing a resistance against antibiotics such as ampicillin and tetracycline, and a sequence necessary for replication in E.coli.

2. Transfer Gene

In the present invention, sarcoglycan (SG) gene is used as a transfer gene. α-, β-, γ- and δ-SG genes are known as SG gene, and any of them may be used. Preferably, δ-SG gene is used. The origin and source of δ-SG gene are not particularly limited, and those derived from any animal can be used. Preferred is δ-SG gene derived from mammal, more preferably from rodent such as hamster, rat or mouse or primate such as monkey or human, further preferably from hamster or human, particularly preferably from human.

Cloning of DNA of α-, β-, γ- and δ-SG derived from hamster and human are described in A. Sakamoto, et al., Proc.Natl.Sci.Acad.U.S.A. 94, 13873 (1997); V. Nigro, et al., Hum.Mol.Genet. 6, 601 (1997);and V. Nigro, et al., Hum.Mol.Genet. 5, 1179 (1996). For example, for the purpose of cloning of δ-SG derived from hamster, cDNA library from golden hamster hearts is constructed in λ ZAP II phage vector, and is screened by using cDNA fragment of human δ-SG (V. Nigro, et al., Hum.Mol.Genet. 5, 1179 (1996)), thereby the cloning can be achieved. Also, cDNA of hamster δ-SG is registered in the database of GenBank as accession Nos. AB001508.

3. Gene Expression Vector

In the gene expression vector of the present invention, it is preferred that a control nucleic acid sequence such as promoter is operatively linked to SG gene. In order to achieve a desired expression level and a heart specific expression, various promoter/enhancer elements can be used. Promoters derived from the genome of mammal cells or promoters obtained by recombinant DNA technique or DNA synthesis technique may be used to carry out transcription of the transferred gene. The promoters include eukaryote promoter such as CMV promoter, pol III (for example, tRNA) promoter, SV40 later promoter, or SV40 early promoter, and SG gene is arranged under the control of these promoters. Also, the promoter may be a heart tissue specific promoter.

Moreover, it is preferred that 3' end of transfer gene contains poly A sequence such as internal poly A sequence of each gene. By adding such a sequence, stabilization of mRNA in cardiac muscle cells can be realized (Jackson, R. J. (1993) Cell 74,9–14; and Palmiter, R. D. et al. (1991) Proc.Natl.Acad.Sci. USA 88, 478–482)

In order to obtain eukaryotic expression vector, standard recombinant DNA techniques may be used. These techniques include in vitro recombinant DNA technique, synthesis technique, and in vivo recombinant/gene recombinant techniques. For example, the methods described in Maniatis et al., 1989 Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y., may be referred.

For example, AAV virus sequence may be amplified by a PCR reaction using oligonucleotide primers which add an appropriate restriction endonuclease recognition site to each end of the amplified virus DNA fragment. Alternatively, any desired digestion site may be obtained by ligation of a nucleotide sequence which encodes a restriction endonuclease sequence to both ends of the amplified target sequence. This target sequence may be then inserted into an expression vector having complementary sticky ends.

A recombinant gene expression vector containing AAV sequence may used as a template for mutagenesis well-known to those skilled in the art so as to prepare a further altered gene expression vector. The mutagenesis includes site-directed mutagenesis, construction of deletion mutant, and the use of PCR for altering the aforementioned AAV sequence, but are not limited thereto.

4. Preparation of Stock of Recombinant Virus

In order to prepare a stock of recombinant virus, the recombinant vector constructed above is tranfected to a host cell line which can provide a helper virus function and can provide REP and CAP proteins of AAV in a trans position. The REP and CAP proteins are necessary for replication of linear recombinant DNA and encompassment of capsid into mutated virus particles, and can be provided in a trans position by transfecting a host cell line with a recombinant plasmid containing genes encoding REP and CAP proteins. DNA transfection can be carried out by using any method well-known to those skilled in the art, and as a result, a transient or continuous expression of REP and CAP proteins is carried out. Methods for performing transfection of DNA into host cells include DNA transfection such as lipofection, electroporation, or calcium phosphate method (Ausubel et al., 1989, Current Protocols for Molecular Biology).

Host cell line must be able to provide an expression of virus REP and CAP proteins as well as helper virus function. As a helper virus for replication of DNA fragment containing AAV target sequence, an adenovirus and a simple herpes virus are both useful. In the practice of the present invention, any host cell may be used which permit infection by either of these two viruses or any virus which functions as a helper virus of AAV. The helper virus which can be used includes simple herpes virus (HSV), zone herpes varicella zoster, cytomegalovirus, and Epstein-Barr virus, but are not limited thereto. The multiplicity of infection and maintaining property of infection period may depend on the types of virus to be used and the cell line to be used.

For example, a recombinant gene expression vector containing SG gene (vector plasmid) can be transfected to a host cell together with a helper plasmid. In such a case, rep and capsid proteins of AAV act in trans to promote replication and packaging of recombinant AAV constructs. On 3 days after transfection, a recombinant AAV virus is collected from cells together with an adenovirus. The adenovirus which has been contained can be inactivated by heat treatment.

5. In vivo Administration of Gene Expression Vector

Transfer of a foreign gene into somatic cells can be performed by AAV into differentiated static cells, and this is particularly suitable for gene therapy of the heart. In vivo long continuous gene expression is ensured by integration ability of AAV gene expression vector, and it is particularly suitable. Further advantage of AAV is that this virus does not become a pathogen to human and is relatively safe in vivo.

(B) Pharmaceutical Composition Comprising A Gene Expression Vector

According to another aspect of the present invention, there is provided a pharmaceutical composition for gene therapy which comprises the gene expression vector of the present invention, particularly a pharmaceutical composition for gene therapy which is used for the therapy of dilated cardiomyopathy.

The form of the pharmaceutical composition is not particularly limited, and include, for example, a pharmaceutical composition which contains a gene expression vector of the present invention in a pharmaceutical carrier composed of a physiological buffer having a pH of preferably about 6.0–8.0, more preferably about 6.5–7.5 and/or an osmol concentration of about 200–400 miliosmol/liter (mosm/L), preferably about 290–310 miliosmol/liter (mosm/L). The pharmaceutical carrier may contain other suitable stabilizers (for example, nuclease inhibitor), chelating agents (for example, EDTA), and/or other assistants.

Alternatively, the pharmaceutical composition of the present invention may be provided as a complex of a gene expression vector containing SG gene and liposome. In such a form, a high transfection efficiency may be achieved especially in cardiac muscle cells. In lipofection, a vesicle of single layer composed of cation charged lipid is formed by supersonic treatment of liposome suspension. DNA is bound to the surface of liposome via ion binding, and is bound in such a way that a positive net charge remains so that 100% of DNA of gene transfer vector is combined with liposome to form complex. Many new lipid formulation such as lipid mixture DOTMA (1,2-dioleoyloxypropyl-3-trimethylammonium bromide) and DOPE (dioleoyl phosphatidylethanolamine) are synthesized, and are tested as to transfection efficiency in various cell lines (Behr, J. P. et al. (1989) Proc.Natl.Acad.Sci.USA 86,6982–6986; Felgner, J. H. et al.(1994) J.Biol.Chem. 269, 2550–2561; Gao, X. & Huang, L.(1991) Biochem.Biophys.Res. Commu.179, 280–285; Zho, X. & Huang, L.(1994) Biochem.Biophys. Acta 1189,195–203). Preparation of DNA-liposome complex and its application in the heart specific transfection are described in, for example, DE 4411402.

The gene expression vector or the pharmaceutical composition containing the same as mentioned above can be applied by using, for example, catheter. Suitably, for example, the expression vector of the present invention or the pharmaceutical composition containing the same is directly injected into the coronary artery of a patient (percutaneous coronary artery gene transfer, PCGT). For example, it is particularly preferred that application is performed with balloon catheter as described in Feldman et al.(Feldman, L. J. et al. (1994) JACC 235A, 906–34), since transfection is limited to the heart in this method.

The amount for administration of the pharmaceutical composition of the present invention should be appropriately changed depending on the conditions such as age, sex, body weight and symptom of a patient, and administration route, and are generally within the range of about 1 μg/kg to 1000 mg/kg, preferably about 10 μg/kg to 100 mg/kg as an amount of DNA which is an active ingredient per administration for adult person. The administration frequency is not particularly limited. When one administration can continue the therapeutic effect, multiple administrations are not necessary. Since a gene expression vector which is integrated into AAV vector could continue expression during ⅔ of the whole life period of the animal in the animal experiment in the following examples below, it is not necessary that the gene expression vector or the pharmaceutical composition containing the same according to the present invention is so frequently administered.

The present invention will be described by the following examples more specifically, but the scope of the present invention is not limited by the examples.

EXAMPLES

Example 1

Gene Transfer of δ-SG

TO-2 hamsters with the early onset of DCM were used as a model animal (T. Kawada, et al., F.E.B.S.Lett. 45, 405 (1999); T. Kawada, et al., Biochem. Biophys.Res.Commun. 259, 408 (1999)). Normal hamster and TO-2 hamster were purchased from Biobreeder (Fitchburg, Mass.).

In the present invention, recombinant adeno-associated virus vector (rAAV) was used as the gene transfer vector, because the vector has been proven to be safe in both experimental animals and humans (P. D. Robbins, S. C. Ghivizzani, Pharmacol.Ther. 80, 35 (1998); J. A. Wagner, et al., Lancet 351, 1702 (1998)). The rAAV containing reporter gene (Lac Z) or normal hamster δ-SG genes were constructed. pW1 (rAAV plasmid) was constructed which contains LacZ reporter gene adjacent to ITR sequence of AAV genome containing rep and cap proteins. A cDNA fragment of δ-SG was inserted in place of the N-terminal half of LacZ gene of pW1.

The rAAV-Lac Z were constructed by using adenovirus-free system (D. S. Fan, et al., Hum.Gene Ther. 9, 2527 (1998)). pWSG harboring the δ-SG expression cassette driven by the CMV promoter was used for rAAV-δ-SG production. For gene transfer experiments, rAAV containing Lac Z or the normal δ-SG gene (1.2 kb) was produced by transfection of 293 cells with a vector plasmid, a helper plasmid (PHLP 19) having rep and cap genes, and pladeno-1 harboring the adenovirus E2A, E4 and VA genes.

rAAV containing LacZ as a marker, and rAAV containing δ-SG gene were injected twice at the same time into the forepart of the heart after thoracotomy of 5 weeks old hamsters (each 15 μl, $8.4 \times 10^{10}$ copies and $6 \times 10^{10}$ copies in total for LacZ and δ-SG respectively).

Ten weeks after the injection of transfer gene, the experiment animals were sacrificed, and the analysis of northern blot, immunostaining of β-Gal and 4 types of SG proteins as well as pathological test were carried out as follows.

Example 2

Northern Blot Analysis

Northern blot analysis were carried out in a conventional way (A. Sakamoto, et al., F.E.B.S.Lett. 447, 124 (1999)). The results are shown in FIG. 1A. As is understood from FIG. 1A, two major transcripts of δ-SG derived from exon 1A and 1B were detected at 1.4 kb and 9.5 kb, respectively, in the heart of control hamster (FIG. 1A, lane C), both of which were missing in TO-2 hamster which loses δ-SG gene in its genome and does not receive an administration of transfer gene (FIG. 1A, lane T, A. Sakamoto, et al., Proc.Natl.Sci.Acad.U.S.A. 94, 13873 (1997); V. Nigro, et al., Hum.Mol.Genet. 6, 601 (1997)). In the heart of TO-2 hamster where δ-SG gene is transduced, while on the other hand, a single robust transcript was present at 4.4 kb (FIG. 1A, lane T+). From these results, it has been found that the rAAV-mediated transgene (δ-SG) was expressed in a broad region with an appreciable amount.

Furthermore, rAAV vector was intramuscularly administered to the hearts of TO-2 hamsters. Cryostat sections which were sampled at 10 weeks after the administration were stained with hematoxylin-eosin to carry out histological examination (FIG. 1B). As is understood from FIG. 1B, inflammatory reaction, including infiltration of polymorphonuclear cells, fibrosis or angiogenesis, were not induced.

Example 3

Confirmation of Production of β-Gal

Figure 2:
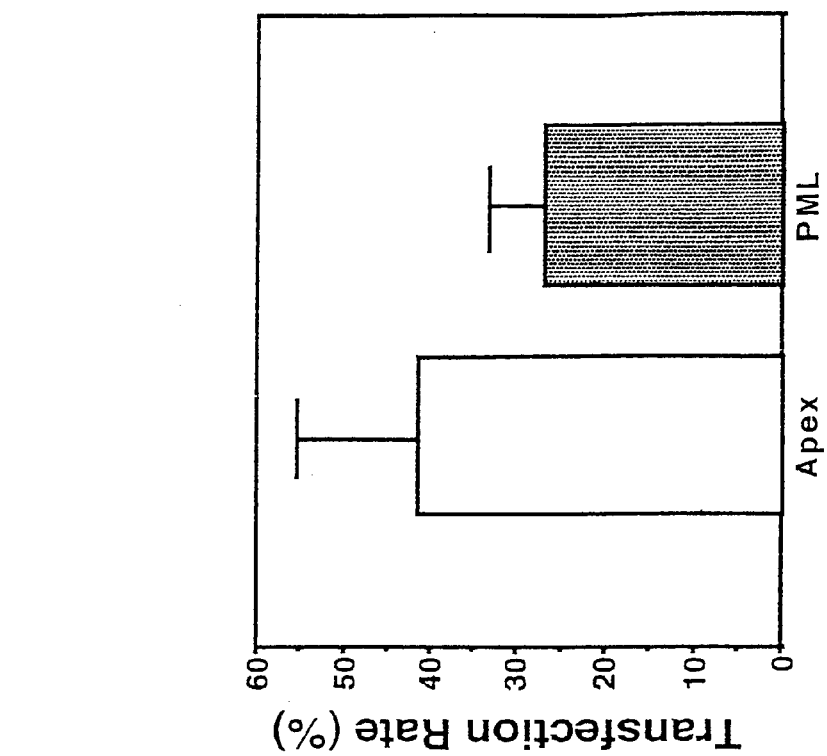
FIG. 2(A) is a diagrams which shows an efficient expression of reporter (β-Gal) at 10 weeks after the rAAV-mediated Lac Z gene transfer to the apical portion of TO-2 hamster hearts. The gene transfer of Lac Z was demonstrated by immunostaining of β-Gal protein which is more sensitive than the histochemical staining when specific antibody is employed (P. D. Robbins, S. C. Ghivizzani, Pharmacol. Ther. 80, 35 (1998); J. A. Wagner, et al., Lancet 351, 1702 (1998)). The area of positive cytoplasm for β-Gal and whole left ventricular wall including intraventricular septum were measured by planimetry for the assay of transduction efficiency. Sample was obtained from cross section at the apex or papillary muscle level (PML, bar=1 mm, original magnification, ×12.5).
FIG. 2(B) represents the β-Gal expression area at the apex where rAAV containing Lac Z gene was locally injected and at the PML.
Figure 2:
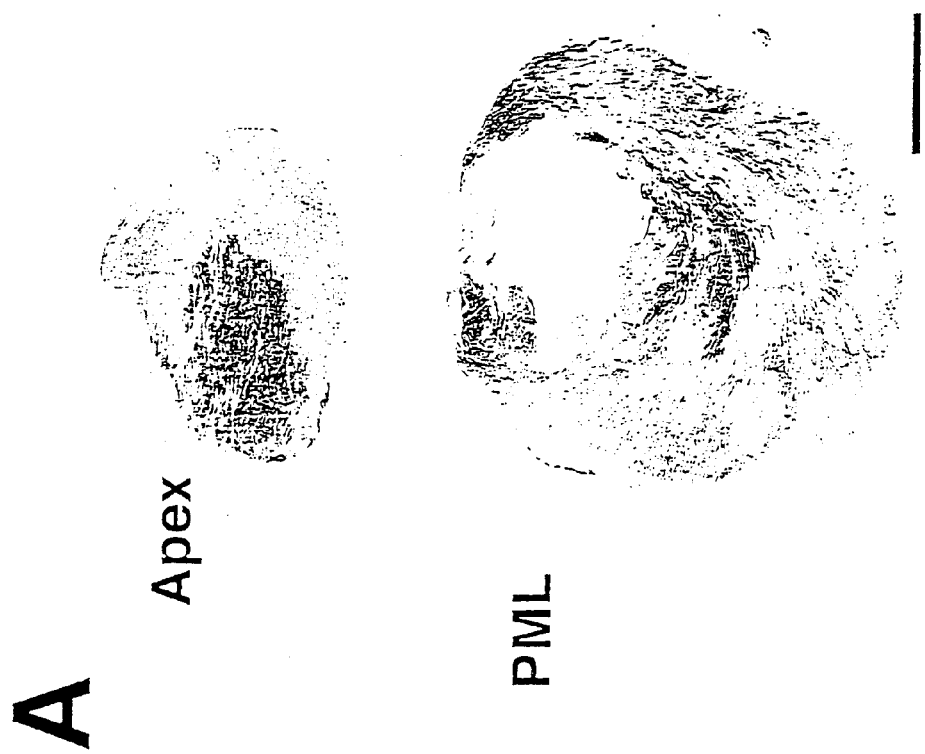

A monoclonal antibody to β-Gal (purchased from Novocastra, Newcastle, England or Funakoshi, Tokyo, Japan) was used to confirm the production of β-Gal (FIGS. 2A and 2B). The β-Gal expression reached a plateau at 10 weeks after the in vivo injection of rAAV (J. P. Greelish, et al., Nature Med. 5, 439 (1999)). The expression efficiency of β-Gal was excellent (FIG. 2A) and the β-Gal expressing cells occupied 41.5±13.6% of total cells in the apex where the vectors were injected, and 27.0±5.9% in a cross section at the papillary muscle level (PML, FIG. 2B), reflecting the infiltration of vector medium or lymphatic flow.

Wall thickness transfected by δ-SG gene became locally wide (FIG. 2A). The β-Gal expressing cells coincided with those cells with δ-SG transgene (FIG. 3A, β-Gal and δ). The transgene was documented after 20 weeks also (data not shown), indicating the transgene was continuously expressed for long period (M. J. Sole, Hamster Inf. Serv. 8, 3 (1986)).

Thus, it was found that rAAV-mediated gene transfer was much superior to other vectors in both the duration and the expression extent.

Example 4

Figure 3:
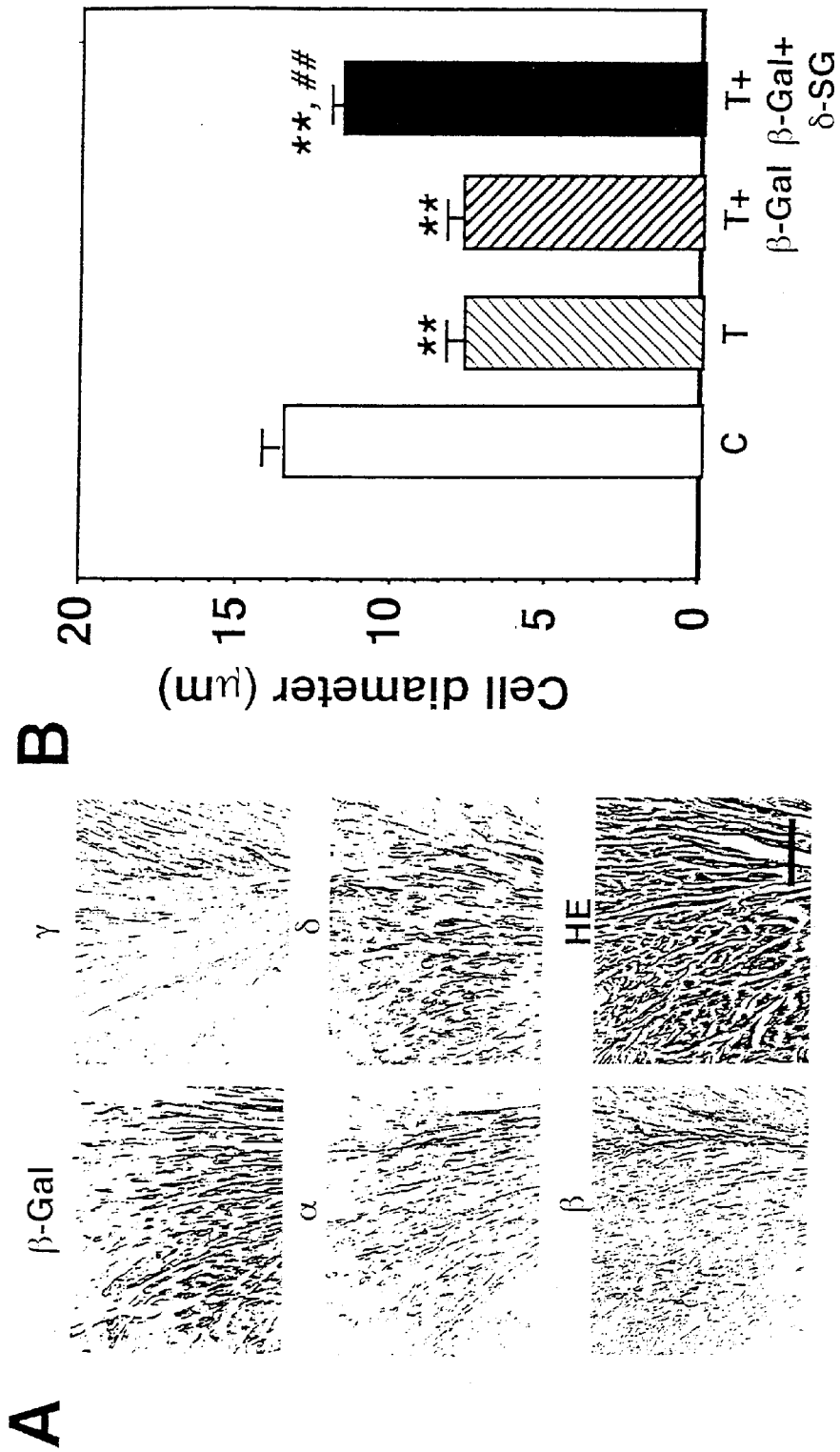
FIG. 3(A) represents the results of immunostaining for the reporter (β-Gal), α-, β-, γ- and δ-sarcoglycan (SG) 10 weeks after the cotransduction of Lac z and δ-SG genes into TO-2 hearts, and the results of histological examination by hematoxylin-eosin (HE) stain (bar=200 mm; original magnification, ×100).
FIG. 3(B) represents caliber of myocardial cells of control hamsters (C), TO-2 hamster (T), transfected in vivo by reporter gene (Lac Z) alone (T+βGal) or together with normal δ-SG gene (T+βGal+δ-SG). The asterisk and # indicate statistically significant (p<0.01) difference, compared with C and T+Lac Z, respectively.

Expression of β-gal and Various SGs and Recovery of Cell Caliber after In Vivo Transduction of δ-SG Gene When Lac Z gene was solely injected to TO-2 hamster heart, the transgene (β-Gal) was exclusively detected in cytoplasm of cardiomyocytes (data not shown), but no SG was detected, as was the case in HVJ liposome-mediated gene transfer (T. Kawada, et al., FEBS.Lett. 45, 405 (1999); T. Kawada, et al., Biochem.Biophys.Res.Commun. 259, 408 (1999)). Therefore, the presence or absence of expression of each of SGs after transduction with the normal δ-SG gene was determined with antibodies. Polyclonal antibody to δ-SG was prepared and purified by an affinity chromatography. Monoclonal antibodies to α-, β- or γ-SG were obtained from Novocastra, Newcastle, England or Funakoshi, Tokyo, Japan. Immunostaining was carried out as described previously (H. Kawaguchi, et al., Circulation 95, 2441(1997)). The results of immunostaining are shown in FIG. 3A. As is understood from FIG. 3, after transduction with the normal δ-SG gene, not only δ-SG, but all the other SGs (α-, β- and γ-SGs) were clearly detected in myocardial cells. The reexpression of each SG was not restricted to sarcolemma but the cytoplasm was also partially stained.

Same phenomena were reported in cardiac or skeletal muscle (T. Kawada, et al., F.E.B.S.Lett. 45, 405 (1999); T. Kawada, et al., Biochem.Biophys.Res.Commun. 259, 408 (1999); J. Li, et al, Gene Therapy 6, 74 (1999)), and suggest complex protein traffic after the biosynthesis of SGs. Another explanation might be supranormal expression of SG protein after a sufficient gene delivery. It should be intensified that any abnormal reaction such as inflammation was not detected in the site where gene was transfected as shown in this Example (FIG. 1B, FIGS. 3A,H,E).

Caliber of myocardial cells with or without the transduction of δ-SG gene was measured in the same specimen. To identify the effect of gene transduction on the atrophic cardiomyocytes and avoid the sampling error, the cell diameter was randomly recorded in both the transduced and untransduced regions. For comparison of the control and DCM cardiomyocytes, 40 cells of 4 hamster hearts (160 cells in total) were randomly selected and measured. The results were shown in FIG. 3B.

Muscle diameter in TO-2 hamster hearts was significantly thicker with the δ-SG transgene than that of untransduced cells (11.7±0.2 mm vs. 7.73±0.17 mm, $p<0.01$). It is clear that the 1.5 folds increment of the cell diameter was not caused by manipulation during the gene therapy, because there was no significant difference between the transduced and non-transduced cardiomyocytes by Lac Z transfer alone (7.81±0.33 mm; 7.71±0.26 mm).

Though the gene therapy with δ-SG was effective to improve these morphological alterations as described above, the gene transfer of δ-SG could not completely heal the pathological changes of DCM, because the diameter (13.6±0.5 mm) of the cardiomyocytes in normal hamster is larger than that of DCM hamster.

Example 5

The Effect of In Vivo Gene Transfer of δ-SG into TO-2 Hamster Heart on Calcification Local calcification is intrinsic to the deletion of δ-SG gene (F. Homburger, J. R. Baker, C. W. Nixon, R. Whitney, Med. Exp. 6, 339 (1962); E. Bajusz, Am.Heart J. 78, 202 (1969)). Similar phenomenon was demonstrated in transgenic mouse heart lacking the δ-SG gene (R. Carol-Verazques, et al., Cell 98, 465 (1999)).

In order to examine the effect of in vivo gene transfer of δ-SG on calcification, score was measured. For the semi-quantification of tissue calcification, scores were determined depending on the degree as follows;
point 0: without calcified region,
point 1: with one calcified spot,
point 2: with two regions and
point 3: with 3 or more regions and/or huge, elongated or fused region.

The score was summed in four cross sections between the injected apex and mitral annulus.

Figure 4:
FIG. 4(A) represents myocardial calcification of TO-2 without in vivo gene transfer of δ-SG.
FIG. 4(B) represents myocardial calcification of TO-2 with in vivo gene transfer of δ-SG for 10 weeks. Arrow marks indicate calcified lesions. Bar length indicates 1 mm.
FIG. 4(C) represents calcification score in control hamster hearts (C), and in TO-2 hamster (T) with in vivo gene transfection of reporter gene (Lac Z) alone or cotransfection with normal δ-SG gene. The asterisk and # indicate statistically significant (p<0.01) difference, compared with C and T+Lac Z, respectively.

The results are shown in FIGS. 4A and 4B. Scores which was calculated in cross sections at the apical level and papillary muscle level (FIG. 4A) were counted in each animal and summed. The hearts of TO-2 hamster transduced by the Lac Z gene alone showed about 3.2 folds larger score than the hamsters treated by both Lac Z and δ-SG genes (8.4+0.9 vs. 2.6+0.6, $p<0.01$, FIG. 4B). These data confirm the idea that loss of δ-SG gene causes calcification.

Example 6

Improvement of Heart Function by In Vivo Administration of δ-SG Gene into TO-2 Hamster Hemodynamic indices were measured adjusting the age (15 weeks old) of animals after the gene transfer. At first, hamsters were anesthetized with 2% isoflurane (Dainippon Pharmaceutical, Osaka, Japan). The CVP (central venous pressure), LVP (left ventricular pressure), LVEDP (left ventricular end-diastolic pressure) and dP/dt were determined by heparin-saline filled polyethylene catheter connected to pressure transducer (A154, Fukuda Denshi, Tokyo, Japan) and catheter-tip pressure transducer (SPR-671, Millar Instruments, Houston, Tex.). Before the measurements, the concentration of isoflurane was reduced to 1% and maintained for 20 min to stabilize the hemodynamics (S. Hirono, et al., Circ. Res. 80, 11 (1997)). These hemodynamic parameters after A/D transduction were recorded on Power Lab system (AD Instruments, Castle Hill, Australia) at 1 kHz.

TO-2 strain revealed lower levels than normal hamster in the left ventricular pressure (LVP) (100±5 mmHg vs. 133±6 mmHg), the maximal derivative of the LVP (dP/dtmax) (4895±303 mmHg/sec vs. 8188±743 mmHg/sec, p<0.01), the minimal derivative of the LVP (dP/dtmin)(−3664±378 mmHg/sec vs. −7118±971 mmHg/sec, p<0.01) and higher values of both left ventricular end-diastolic pressure (LVEDP) (8.82±1.92 mmHg vs. 1.84±1.48 mmHg, p<0.01) and central venous pressure (CVP) (2.70±0.87 mmHg vs. 0.78±0.50 mmHg, p<0.05), and showed no significant change in heart rate (HR)(382±20 beats/min vs. 377±9 beats/min).

Physical parameters showed a reduced body weight (103±1 g vs. 122±3 g, p<0.01), a reduced heart weight (294±7 mg vs. 382±11 mg, p<0.01) and a reduced heart weight/body weight ratio (0.284±0.005, vs. 0.314±0.007%, p<0.01) in TO-2 strain, compared with the normal strain.

These results indicate the lowered systolic and diastolic function as well as congestive heart failure in both left and right ventricles in TO-2 strain.

Figure 5:
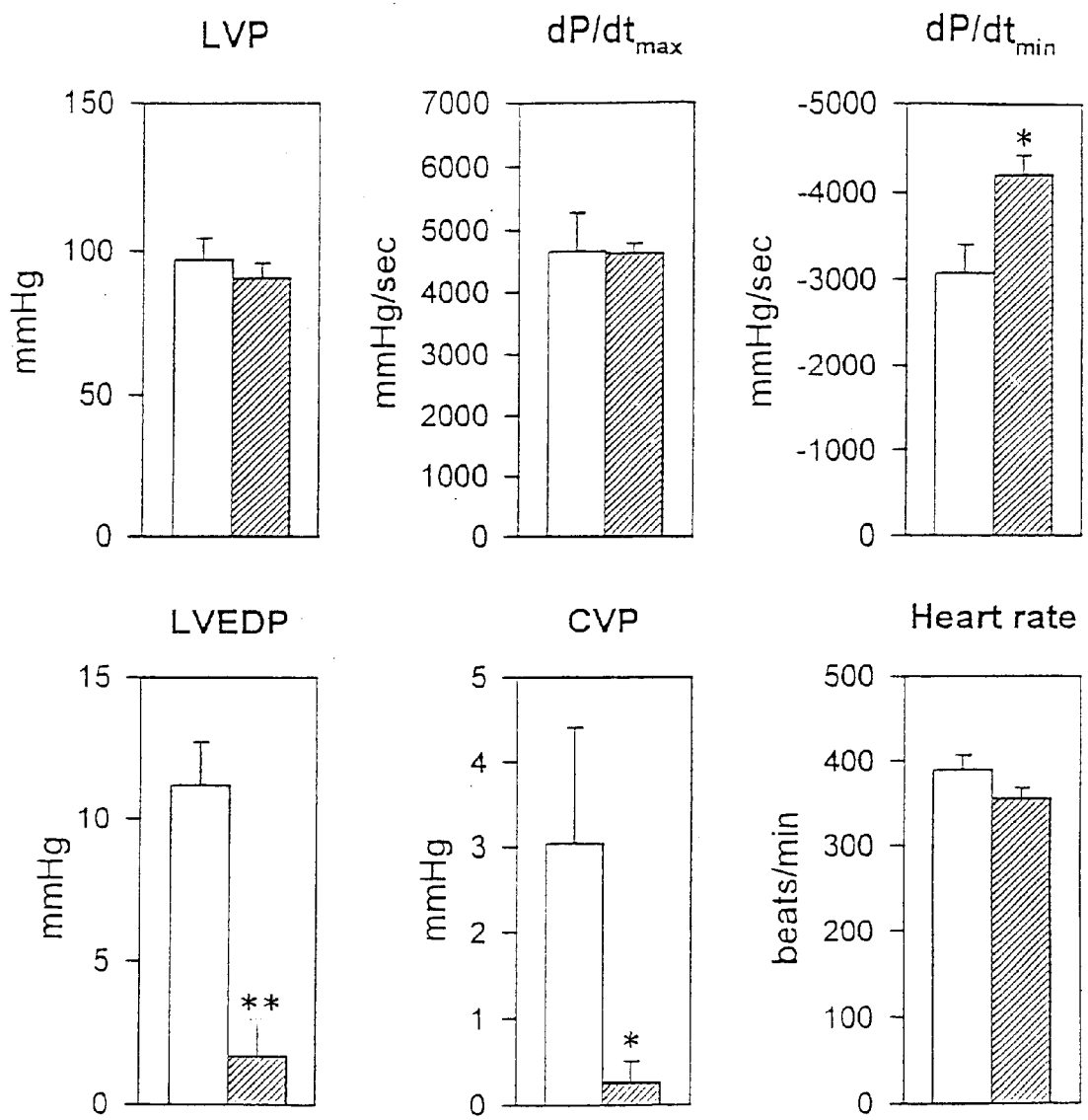
FIG. 5 represents improvement of hemodynamic parameters after the in vivo gene transfer of δ-sarcoglycan (SG). Open bar denotes TO-2 hamsters transduced for 10 weeks with the reporter (Lac Z) alone, and hatched bar denote TO-2 hamsters transduced for 10 weeks with the reporter (Lac Z) and δ-SG genes. The asterisk indicates the statistical significance, compared with the transduction of Lac Z alone at p<0.05 (*) and p<0.01 (**) level, respectively.

Then, the effect of δ-SG gene transduction in vivo on these hemodynamic indices was evaluated. The results are shown in FIG. 5.

In TO-2 hamsters which were subjected to cotransduction of δ-SG gene and Lac Z gene, the dP/dtmin was improved from −3072±331 mmHg/sec to −4202±229 mmHg/sec (p<0.05), the LVEDP was improved from 11.2±1.5 mmHg to 1.6±1.3 mmHg (p<0.01), and the CVP was improved from 3.04±1.36 mmHg to 0.25±0.24 mmHg (p<0.05), as compared with the hamsters transduced with Lac Z gene alone.

However, the LVP is 97.0±7.7 vs. 90.7±5.0 mmHg, and the dP/dtmax is 4645±637 mmHG/sec vs. 4623±157 mmHg/sec, and the HR is 390±18 beats/min vs. 356±13 beats/min, respectively. These parameters showed no significant change.

Discussion of Example

From the results above, it has been found that the gene therapy preferentially improved at first the diastolic function and congestion of both left and right ventricles than the systolic performance. Diastolic function is mainly determined by $Ca^{2+}$ uptake from myoplasm to sarcoplasmic reticulum or extracellular space using $Ca^{2+}$ ATPase (S. Ebashi, Y. Nonomura, T. Toyo-oka, E. Katayama, Symp. Soc.Exp.Biol. 30, 349 (1976); M. Endo, Physiol.Rev. 57, 71 (1977)). Free $Ca^{2+}$ level in diastole is elevated in DCM hamster heart as well as human myocardial cells in heart failure (J. K. Gwathmey, et al., Circ.Res 61, 70 (1987); M. J. Lab, J. A. Lee, Circ.Res. 66, 585 (1990); C. L. Pereault, R. P. Shanoon, K. Komamura, S. F. Vatner, J. P. Morgan, J.Clin.Invest. 89, 932 (1992)), reflecting the depletion of energy supply (T. Toyo-oka, H. Arisaka, T. Takayasu, T. Tezuka, S. Hosoda, Prog.Clin.Biol.Res. 315, 567 (1989); T. Toyo-oka, J.Mol.Cell.Cardiol. 5, 141 (1989); T. Toyo-oka, K. Nagayama, J. Suzuki, T. Sugimoto, Circulation 86, 295 (1992)).

Forceful contraction of skeletal muscle of BIO 14.6 hamster (a model animal of hypertrophied cardiomyopathy) increased $Ca^{2+}$ influx and induced proteolysis of dystrophin (V. Staub, et al., Am.J.Pathol. 153, 1623 (1998)). Cardiac muscle as well as skeletal muscle endogenously contain calcium-activated neutral protease (calpain, R. B. Huston, E. G. Krebs, Biochemistry 6; 2116 (1968); W. R. Dayton, et al., Biochemistry 15, 2150 (1976); W. R. Dayton et al., Biochemistry 15, 2159 (1976); T. Toyo-oka, T. Shimizu, T. Masaki, Biochem.Biophys.Res.Commun. 82, 484(1978); T. Toyo-oka, T. Masaki, J.Mol.Cell. Cardiol. 11, 769 (1979)) and is destined to continue the beating. $Ca^{2+}$ ions enter to myoplasm during slow inward current and should be excreted outward with active transport. Myocardial cells might be more fragile to the repeated contraction than skeletal muscle which does not obligatorily repeat the contraction. Cardioselective $Ca^{2+}$ entry blocker (verapamil) has been shown to be beneficial for the treatment of not only cardiomyopathic hamsters but human cases with hypertrophic cardiomyopathy (A. Fleckenstein, et al., in Pathophysiology and morphology of myocardial alterations. pp. 21–47. A. Fleckenstein, G. Rona, eds., (University Park Press, Baltimore, 1975); M. Kaltenbach, et al., Br.Heart J. 42, 35 (1979)).

Though the gene expression site did not cover whole heart (FIG. 2), this tentative gene therapy was strikingly effective to ameliorate the diastolic function. These data might imply that local improvement of the contractility may alter not only total ventricular performance but also neurohumoral factors (T. Toyo-oka, et al., Circulation 83, 476 (1991); T. Toyo-oka, T. Sugimoto, Circulation 84, 1451 (1991); W. S. Shin, et al., Ann.N.Y.Acad.Sci. 786, 233 (1996)), and autacoids and/or cytokines (J. Narula, et al., New Engl. J.Med. 335, 1182 (1996); F. M. Habib, et al., Lancet 347, 1151 (1996); G. Olivetti, et al., New Engl.J.Med. 336, 1131 (1997); H. Hikiji, et al., F.E.B.S.Lett. 410, 238 (1997); H. Hikiji, et al., Am.J.Physiol. in press). This is similar to the Batista's procedure for the temporary enhancement of subjective and objective findings (R. C. Starling, J. B. Young, Cardiol.Clin. 16, 727 (1998); R. Batista, Eur.J.Cardiothorac. Surg. 15 (Suppl.1),. S12 (1999); R. SoRelle, Circulation 99, 845 (1999)).

Gene defect and the corresponding protein disruption in one of these components commonly induces muscle degeneration, accompanying cardiac symptoms. In fact, gene mutation of cardiac F-actin, dystrophin, each SG, laminin-2 and lamin A/C causes dilated cardiomyopathy in human cases as the chief symptom or a partial sign (T. M. Olson, et al., Science 280, 750 (1998); D. Fatkin, et al., New Engl.J.Med. 341, 1715 (1999)). Interruption between intracellular F-actin and extracellular laminin-2 would fail to preserve the integrity of sarcolemma and finally lead to dilated cardiomyopathy, though mutation of lamin A/C do not explain the precise mechanism leading to the muscle degeneration.

Furthermore, acquired case after enterovirus infection shows dilated cardiomyopathy-like symptom due to the selective cleavage of dystrophin by protease 2A translated from the virus gene (C. Badorff, et al., Nature Med. 5, 320 (1999)). Thus, the disruption may cause cardiac failure irrespective of the pathogenesis of gene deficiency.

Industrial Applicability

By administering the gene expression vector of the present invention to a living body in vivo, a sarcoglycan can be continuously expressed in the living body, so that the restoration of α-, β-, γ- and δ-sarcoglycan components can be accompanied and the heart function of the patient of dilated cardiomyopathy can be improved.

The gene expression vector of the present invention has advantages that it is free from infectivity and pathogenicity and is safe, and that it has a high gene transfer efficiency and a high gene expression efficiency, and frequent administration is not necessary.

Thus, according to the present invention, it has become possible to provide a novel strategy for the treatment of congestive heart failure with using somatic gene therapy.

What is claimed is:

1. A method for treating a patient suffering from dilated cardiomyopathy caused by deletion of δ-sarcoglycan gene, which comprises directly injecting into the heart muscle of said patient an adeno-associated virus (AAV) vector encoding the δ-sarcoglycan protein.

2. The method according to claim 1 wherein the inserted sarcoglycan gene is a hamster or human sarcoglycan gene.

3. A method for treating a patient suffering from dilated cardiomyopathy caused by deletion of α-sarcoglycan gene, which comprises directly injecting into the heart muscle of said patient an adeno-associated virus (AAV) vector encoding the α-sarcoglycan protein.

4. The method according to claim 3 wherein the inserted sarcoglycan gene is a hamster or human sarcoglycan gene.

5. A method for treating a patient suffering from dilated cardiomyopathy caused by deletion of β-sarcoglycan gene, which comprises directly injecting into the heart muscle of said patient an adeno-associated virus (AAV) vector encoding the β-saroglycan protein.

6. The method according to claim 3 wherein the inserted sarcoglycan gene is a hamster or human sarcoglycan gene.

7. A method for treating a patient suffering from dilated cardiomyopathy caused by deletion of γ-sarcoglycan gene, which comprises directly injecting into the heart muscle of said patient an adeno-associated virus (AAV) vector encoding the γ-saroglycan protein.

8. The method according to claim 3 wherein the inserted sarcoglycan gene is a hamster or human sarcoglycan gene.

* * * * *

UNITED STATES PATENT AND TRADEMARK OFFICE
CERTIFICATE OF CORRECTION

PATENT NO. : 6,589,523 B2
DATED : July 8, 2003
INVENTOR(S) : T. Toyo-Oka

It is certified that error appears in the above-identified patent and that said Letters Patent is hereby corrected as shown below:

<u>Column 14,</u>
Lines 7 and 14, "saroglycan" should be -- sarcoglycan --.
Line 8, "3" should be -- 5 --.
Line 15, "3" should be -- 7 --

Signed and Sealed this

Twenty-seventh Day of January, 2004

JON W. DUDAS
*Acting Director of the United States Patent and Trademark Office*